US010864280B2

(12) United States Patent
Tien

(10) Patent No.: US 10,864,280 B2
(45) Date of Patent: Dec. 15, 2020

(54) NANODROPLET COMPOSITIONS FOR THE EFFICIENT DELIVERY OF ANTI-CANCER AGENTS

(71) Applicant: Der-Yang Tien, Pasadena, CA (US)

(72) Inventor: Der-Yang Tien, Pasadena, CA (US)

(*) Notice: Subject to any disclaimer, the term of this patent is extended or adjusted under 35 U.S.C. 154(b) by 0 days.

(21) Appl. No.: 16/308,115

(22) PCT Filed: Jun. 9, 2017

(86) PCT No.: PCT/US2017/366780
§ 371 (c)(1),
(2) Date: Dec. 7, 2018

(87) PCT Pub. No.: WO2017/214468
PCT Pub. Date: Dec. 14, 2017

(65) Prior Publication Data
US 2019/0160182 A1    May 30, 2019

Related U.S. Application Data

(60) Provisional application No. 62/347,695, filed on Jun. 9, 2016.

(51) Int. Cl.
| | | |
|---|---|---|
| *A61K 47/69* | (2017.01) | |
| *A61K 9/00* | (2006.01) | |
| *A61K 47/34* | (2017.01) | |
| *A61K 9/19* | (2006.01) | |
| *A61K 9/107* | (2006.01) | |
| *A61P 35/00* | (2006.01) | |
| *A61K 31/337* | (2006.01) | |
| *B82Y 5/00* | (2011.01) | |

(52) U.S. Cl.
CPC ........ *A61K 47/6907* (2017.08); *A61K 9/0019* (2013.01); *A61K 9/1075* (2013.01); *A61K 9/19* (2013.01); *A61K 31/337* (2013.01); *A61K 47/34* (2013.01); *A61P 35/00* (2018.01); *B82Y 5/00* (2013.01)

(58) Field of Classification Search
CPC ........ A61P 35/00; B82Y 5/00; A61K 9/1075; A61K 9/0019; A61K 9/19; A61K 47/34; A61K 47/50; A61K 47/6905; A61K 47/6907; A61K 47/6909
See application file for complete search history.

(56) References Cited

U.S. PATENT DOCUMENTS

| | | | |
|---|---|---|---|
| 6,218,393 B1 | 4/2001 | Ryder et al. | |
| 7,868,172 B2 | 1/2011 | Schiemann et al. | |
| 9,056,111 B1 | 6/2015 | Larson et al. | |
| 2004/0213837 A1* | 10/2004 | Mantripragada | A61K 9/127 424/450 |
| 2005/0106182 A1 | 5/2005 | Li et al. | |
| 2006/0264384 A1 | 11/2006 | Johansen et al. | |
| 2007/0009533 A1 | 1/2007 | Sikic et al. | |
| 2007/0009535 A1 | 1/2007 | Sikic et al. | |
| 2008/0152640 A1 | 6/2008 | Prehm | |
| 2009/0170880 A1 | 7/2009 | Van Tellingen | |
| 2009/0253616 A1 | 10/2009 | Keen | |
| 2009/0324552 A1 | 12/2009 | Lichter et al. | |
| 2010/0041691 A1 | 2/2010 | Weikop et al. | |
| 2010/0189683 A1 | 7/2010 | Holmlund et al. | |
| 2011/0118199 A1 | 5/2011 | Dormeyer | |
| 2011/0177005 A1* | 7/2011 | Rapoport | A61K 9/0009 424/9.37 |
| 2011/0275705 A1* | 11/2011 | Daftary | A61K 9/0019 514/449 |
| 2014/0235631 A1 | 8/2014 | Bunt et al. | |
| 2015/0283246 A1* | 10/2015 | Liu | A61K 47/42 514/34 |
| 2016/0166571 A1 | 6/2016 | Janes et al. | |
| 2016/0303107 A1 | 10/2016 | Trotti et al. | |
| 2017/0151339 A1* | 6/2017 | White | A61K 49/0032 |

OTHER PUBLICATIONS

International Search Report and Written Opinion for PCT/US17/36678 dated Sep. 6, 2017 (12pp).
Gowda et al., "Use of Nanotechnology to Develop Multi-Drug Inhibitors for Cancer Therapy;" 2013, J. Nanomed. Nanotechnol., 4:184 (27pp).
Hu et al., "Nanoparticle-based combination therapy toward overcoming drug resistance in cancer," 2012, Biochem. Pharmacol., 83:1104-1111.
ThePharmaLetter, "QLT and Xenova hit by termination of tariquidar trials in NSCLC," May 19, 2003, <https://www.thepharmaletter.com/article/qit-and-xenova-hit-by-termination-of-tariquidar-trials-in-nsclc> Accessed Dec. 7, 2018, (1pp).
Sutradhar et al., "Nanotechnology in Cancer Drug Delivery and Selective Targeting," 2014, ISRN Nanotech., Article ID 939378 (13pp).
Tang et al., "Recent progress in nanotechnology for cancer therapy," 2010, Chinese J. Cancer, 29:775-780.

* cited by examiner

*Primary Examiner* — H. Sarah Park
(74) *Attorney, Agent, or Firm* — Thomas|Hostemeyer, LLP

(57) ABSTRACT

Disclosed herein are nanodroplet compositions composed of a copolymer with a hydrophilic block and a hydrophobic block, a poloxamer, an oil, an anti¬cancer agent, and optionally a lyoprotectant. The nanodroplet compositions exhibit low toxicity and are biodegradable, provide for slow, sustained release of the anti-cancer agent at tumor sites, and result in a greater reduction of tumor volume when administered to subjects with cancer as compared to several commercially-available products. Furthermore, the nanodroplet compositions can be imaged and their progress through the body tracked with magnetic resonance spectroscopy or ultrasound.

24 Claims, 12 Drawing Sheets

NANODROPLET COMPOSITIONS FOR THE EFFICIENT DELIVERY OF ANTI-CANCER AGENTS

CROSS REFERENCE TO RELATED APPLICATIONS

This application claims priority upon U.S. provisional application Ser. No. 62/347,695, filed Jun. 9, 2016. This application is hereby incorporated by reference in its entirety.

BACKGROUND

Delivery of hydrophobic drugs to the appropriate tissues in the body has long been a challenge for medical researchers, who must maximize biocompatibility while minimizing toxicity. An ideal delivery vehicle would avoid premature release of its cargo, thereby delivering a larger dose of the drug to the effective site. Further, it is highly desirable to avoid affecting non-target tissue in order to maximize treatment of the target area as well as to avoid systemic effects. This is of particular concern in cancer research, where many anti-cancer chemotherapeutic agents are hydrophobic and can have toxic side effects.

Some current solutions to this problem involve liposomes, which have been in use for decades, and more recently, polymeric micelles. Thus far, only NK105 and GENEXOL® PM have been approved for or entered into clinical trials. GENEXOL® PM consists of a monomethoxy poly(ethylene oxide)-poly(D,L-lactide) (mPEG-PDLLA) copolymeric micelle loaded with the anti-cancer agent paclitaxel and has shown activity against breast cancer, non-small cell lung cancer, advanced gastric cancer, and pancreatic cancer. GENEXOL® PM has an mPEG block with a molecular weight of approximately 2000 Da and a PDLLA block with a molecular weight of approximately 1750 Da, with an average particle diameter of 24 nm.

Despite the promise shown by GENEXOL® PM, this treatment is not without problems. The lower molecular weight of the PDLLA in the micelles means that the micelles are in equilibrium in solution with their unimers. As unimers are eliminated (through diffusion or a similar mechanism), more micelles dissociate to maintain this equilibrium. Once the concentration of components drops below the critical micelle concentration (CMC), the micelles disintegrate. Since the paclitaxel in this formulation is associated with the hydrophobic blocks of the unimers, premature drug release occurs. Further, extravasation of unimers into normal tissue occurs more quickly than extravasation of the micelle into tumor tissue, resulting in a decrease in tumor targeting efficiency. Additionally, fast diffusion can result in a concentration gradient induced particle flow from the tumor to normal organs until the drug is equilibrated, which decreases targeting efficiency and may result in systemic effects.

What is needed is a delivery vehicle that results in slower drug release due to increased stability of the vehicle upon dilution during circulation, better tumor growth inhibition, and fewer systemic effects including lower hematological toxicity. Furthermore, compatibility with imaging techniques such as magnetic resonance spectroscopy or ultrasound would be desirable. The present invention addresses these needs.

SUMMARY

Disclosed herein are nanodroplet compositions containing a copolymer with a hydrophilic block and a hydrophobic block, a poloxamer, an oil, an anti-cancer agent, and optionally a lyoprotectant. These nanodroplet compositions exhibit low toxicity and are biodegradable, provide for slow, sustained release of the anti-cancer agent at tumor sites, and result in a greater reduction of tumor volume when administered to subjects with cancer as compared to several commercially-available products. Furthermore, the nanodroplet compositions can be imaged and their progress through the body tracked with magnetic resonance spectroscopy or ultrasound.

The advantages of the materials, methods, and devices described herein will be set forth in part in the description that follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
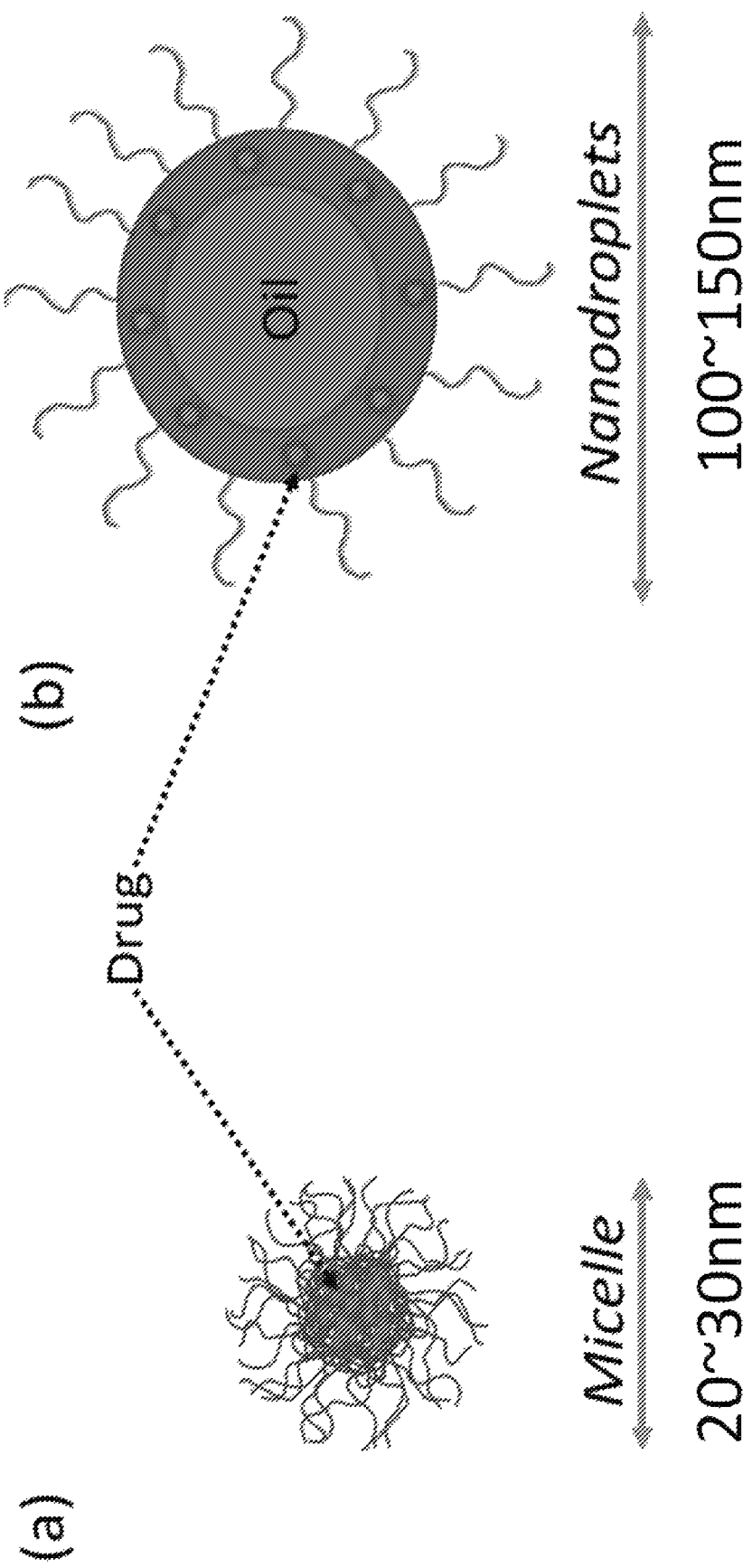
FIG. 1 is an illustration of the different arrangement of constituents in (a) micelles versus (b) nanodroplets as disclosed herein. In each, hydrophilic elements project into solution while hydrophobic elements are at the particle core. Included anti-cancer drugs or other hydrophobic molecules cluster in the hydrophobic areas of the micelles or nanodroplets. The nanodroplets additionally incorporate an oil in the hydrophobic core and have a larger Z-average diameter than the micelles.

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an anti-cancer agent" includes mixtures of two or more such anti-cancer agents, and the like.

"Optional" or "optionally" means that the subsequently described event or circumstance can or cannot occur, and that the description includes instances where the event or circumstance occurs and instances where it does not. For example, the compositions described herein may optionally contain one or more lyoprotectants, where the lyoprotectant may or may not be present.

As used herein, the term "about" is used to provide flexibility to a numerical range endpoint by providing that a given value may be "a little above" or "a little below" the endpoint without affecting the desired result.

Throughout this specification, unless the context dictates otherwise, the word "comprise," or variations such as "comprises" or "comprising," will be understood to imply the inclusion of a stated integer or step or group of integers or steps but not the exclusion of any other integer or step or group of integers or steps. It is also contemplate that the term "comprises" and variations thereof can be replaced with other transitional phrases such as "consisting of" and consisting essentially of."

"Admixing" or "admixture" refers to a combination of two components together when there is no chemical reaction or physical interaction. The terms "admixing" and "admixture" can also include the chemical interaction or physical interaction among any of the components described herein upon mixing to produce the composition. The components can be admixed alone, in water, in another solvent, or in a combination of solvents.

The term "subject" as defined herein is any organism in need of cancer treatment and/or prevention. In one aspect, the subject is a mammal including, but not limited to, humans, domesticated animals (e.g., dogs, cats, horses), livestock (e.g., cows, pigs), and wild animals.

The term "treat" as used herein is defined as maintaining or reducing the symptoms of a pre-existing condition. For example, the compositions described herein are used to treat cancer.

The term "prevent" as used herein is defined as eliminating or reducing the likelihood of occurrence of one or more symptoms of a disease or disorder. For example, the compositions described herein can be used to prevent the regrowth of tumor cells or reduce the rate of regrowth of tumor cells.

The term "inhibit" as used herein is the ability of the compounds described herein to completely eliminate the activity or reduce the activity when compared to the same activity in the absence of the compound. For example, the compositions described herein can be used to inhibit the growth and/or spread of cancers in the body of a subject.

"Biodegradable" materials are capable of being decomposed by bacteria, fungi, or other organisms, or by enzymes in the body of a subject.

"Biocompatible" materials are materials that perform their desired functions without eliciting harmful or deleterious changes to the subject in which they are implanted or to which they are applied, either locally or systemically. In one aspect, the compositions disclosed herein are biocompatible.

As used herein, "toxicity" refers to harmful effects a substance has on an organism such as a human or mammal, or on cells within that organism. A compound or composition with high toxicity would be unsuitable for use as a medical treatment, while a compound or composition with low toxicity would be acceptable for use as a medical treatment. In one aspect, the compounds and compositions disclosed herein exhibit low toxicity.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "alkoxy group" as used herein is defined as RO—, where R is an alkyl group or aryl group defined herein.

The term "halogenated group" is any organic group such as, for example, an alkyl group or aryl group, that possesses at least one halogen (F, Cl, Br, I).

References in the specification and concluding claims to parts by weight, of a particular element in a composition or article, denote the weight relationship between the element or component and any other elements or components in the composition of article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound. A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4, the sub ranges such as from 1-3, from 2-4, from 3-5, etc., as well as 1, 2, 3, 4, and 5 individually. The same principle applies to ranges reciting only one numerical value as a minimum or a maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a poloxamer is disclosed and discussed and a number of different oils are discussed, each and every combination of poloxamer and oil that is possible is specifically contemplated unless specifically indicated to the contrary. For example, if a class of molecules A, B, and C are disclosed, as well as a class of molecules D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the subgroup of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Copolymer

In one aspect, the compositions include a copolymer. In one aspect, the copolymer includes a hydrophilic block and a hydrophobic block. In another aspect, the hydrophilic block can be polyethylene glycol or monomethoxy polyethylene glycol. In still another aspect, the hydrophobic block can be polylactide, a copolymer of lactide and glycolide, a copolymer of D,L-lactide and glycolide, a polycaprolactone, a polyanhydride, or a polyorthoester.

In one aspect, the copolymer is an AB diblock copolymer, wherein A represents the hydrophilic block and B represents the hydrophobic block. In another aspect, the copolymer is an ABA or BAB triblock copolymer where A blocks are hydrophilic and B blocks are hydrophobic.

Hydrophilic Block

In another aspect, the hydrophilic block of the copolymer has a molecular weight of from about 1,000 Daltons to about 3,000 Daltons. In another aspect, the hydrophilic block of the copolymer has a molecular weight of 1,000 Daltons, 1,250 Daltons, 1,500 Daltons, 1,750 Daltons, 2,000 Daltons, 2,250 Daltons, 2,500 Daltons, 2,750 Daltons, or 3,000 Daltons, where any value can be a lower and upper endpoint of a range (e.g., 1,000 Daltons to about 2,500 Daltons, 1,500 Daltons to about 2,500 Daltons). In a further aspect, the hydrophilic block of the copolymer is monomethoxy polyethylene glycol having a molecular weight of from 1,500 Daltons to 2,500 Daltons.

Hydrophobic Block

In another aspect, the hydrophobic block of the copolymer has a molecular weight of from about 1,000 Daltons to about 3,000 Daltons. In another aspect, the hydrophobic block of the copolymer has a molecular weight of 1,000 Daltons, 1,250 Daltons, 1,500 Daltons, 1,750 Daltons, 2,000 Daltons, 2,250 Daltons, 2,500 Daltons, 2,750 Daltons, or 3,000 Daltons, where any value can be a lower and upper endpoint of a range (e.g., 1,000 Daltons to about 2,500 Daltons, 1,500 Daltons to about 2,500 Daltons). In still another aspect, the hydrophobic block of the copolymer is polylactide or poly(D,L-lactide). In yet another aspect, the hydrophobic block of the copolymer is poly(D,L-lactide) having a molecular weight of from 1,500 Daltons to 2,500 Daltons.

Block Copolymer

In one aspect, the hydrophilic or A block of the copolymer is monomethoxy polyethylene glycol having a molecular weight of from 1,500 Daltons to 2,500 Daltons and the hydrophobic or B block of the copolymer is poly(D,L-lactide) having a molecular weight of from 1,500 Daltons to 2,500 Daltons.

Targeting Agents

The use of a targeting agent with the copolymers described herein is also a feature of the composition described herein. In some instances, targeting agents can be chemically bonded to or associated with the copolymer in order to better localize the anti-cancer agent to a specific site in the body or tissue type. In one aspect, such targeting reduces systemic side effects of the anti-cancer agent.

Poloxamers

One or more poloxamers are present in the compositions described herein. As used herein, a "poloxamer" is a nonionic triblock copolymer. The central block in a poloxamer is hydrophobic and comprises polypropylene oxide, while the outer two blocks are hydrophilic and consist of polyethylene oxide chains. Poloxamers are known to self-assemble in a temperature-dependent manner and may, for example, form gels at higher temperatures while remaining liquid at lower temperatures. In some aspects, poloxamers can increase the water solubility of hydrophobic substances.

In one aspect, the poloxamer has the formula

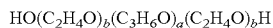

$$HO(C_2H_4O)_b(C_3H_6O)_a(C_2H_4O)_bH$$

wherein a is from 5 to 100, 5 to 50, 25 to 50 or from 25 to 35; b is from 5 to 100, 20 to 100, 50 to 100, 50 to 80, or 70 to 80. In a further aspect a is from 25 to 35 and b is from 70 to 80. In another aspect, the poloxamer has a molecular weight from 2,000 to 15,000, 3,000 to 14,000, or 4,000 to 12,000 Daltons. In another aspect, a is about 29 and b is about 75 and the poloxamer has a molecular weight of about 8,400 Daltons.

In another aspect, the poloxamer has an oxyethylene content of about 70% to about 90%, from 75% to 85%, or from 79.9% to 83.7%.

Poloxamers useful herein are sold under the trade name PLURONIC® manufactured by BASF. In one aspect, PLURONIC® P188 or PLURONIC® P407 can be used as the poloxamer in the compositions disclosed herein.

Oil

The compositions disclosed herein include an oil. An "oil" as used herein is a viscous, hydrophobic liquid. In one aspect, the oil is natural. Further in this aspect, the oil may be extracted from a plant or animal and may be composed of fatty acids and/or fatty acid triglycerides. In another aspect, the oil is petroleum-derived or synthetic or is a mixture of natural and synthetic substances.

In one aspect, the oil is a neutral oil and is stable against oxidation, spreadable, penetration-promoting, and soluble in the compositions and solutions described herein. In another aspect, the oil is a mixture of two or more oils.

In one aspect, the oil includes or contains one or more fatty acid triglycerides, wherein the triglyceride is the reaction product between glycerol and a fatty acid. In one aspect, the fatty acid triglyceride has fatty acid tails from various saturated and/or unsaturated fatty acids. In a further aspect, the fatty acids in the fatty acid triglyceride can be the same or different. In another aspect, the fatty acids can be dicarboxylic acids. In still another aspect, the fatty acids can be natural or can be chemically modified.

Examples of fatty acids include, but are not limited to: butanoic acid, hexanoic acid, caprylic (octanoic) acid, capric (decanoic) acid, dodecanoic acid, tetradecanoic acid, hexadecanoic acid, octadecanoic acid, palmitoleic acid, oleic acid, linoleic acid, α-linoleic acid, arachidonic acid, eicosapentaenoic acid, erucic acid, docosahexanoic acid, succinic acid, or combinations thereof.

In another aspect, the fatty acid has from 4 to 20 carbon atoms. In another aspect, the fatty acid is caprylic acid, capric acid, linoleic acid, succinic acid, a dicaprylate, or a combination thereof.

In one aspect, the oil is a mixture of caprylic triglyceride and capric triglyceride. In another aspect, oils useful herein are sold under the trade name MIGLYOL® from 101 Oleo GmbH. In one aspect, MIGLYOL® 810 or 812 (caprylic/capric triglycerides), MIGLYOL® 818 (caprylic/capric/linoleic triglyceride), MIGLYOL® 829 (caprylic/capric/succinic triglyceride), or MIGLYOL® 840 (propylene glycol dicaprylate/dicaprate) can be used. In one aspect, MIGLYOL® 812 is the oil used in the compositions disclosed herein.

In a further aspect, the oil is a mixture of a halogenated alkyl chain such as, for example, PFOB, and a fatty acid triglyceride. In this aspect, the nanodroplet compositions can be viewed by magnetic resonance spectroscopy or ultrasound imaging techniques. Further in this aspect, the ratio of PFOB to fatty acid triglyceride can be from 1 to 5 or can be from 2 to 4.

Anti-Cancer Agent

The compositions described herein include one or more an anti-cancer agents. As used herein, an "anti-cancer agent" is a compound or composition used in chemotherapy to kill cancer cells in the body of a subject, to slow the growth of cancer in a subject, to keep a cancer from spreading in a subject, or to prevent the return of a tumor that has been surgically removed. Anti-cancer agents may operate by a variety of methods including, but not limited to, by alkylating DNA (which can interfere with coiling and recognition by DNA replication enzymes), by interfering with the production of DNA, by interfering with the production of proteins in cancer cells, by preventing cancer cells from dividing, or by slowing the growth of a cancer that depends on hormones.

The compositions described herein are useful in delivering hydrophobic anti-cancer agents, which assists in the uptake of the anti-cancer agent into the nanodroplets. Any small, hydrophobic molecule can be incorporated into the nanodroplets. In some aspects, additional therapeutic agents such as antiviral drugs or antibiotics can be incorporated into the nanodroplets alone or in addition to one or more anti-cancer agents.

Examples of anti-cancer agent include, but are not limited to, platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbacine, bendamustine), antitumor antibiotics (e.g., daunorubicin, doxorubicin, idarubicin, epirubicin, mitoxantrone, bleomycin, mytomycin C, plicamycin, dactinomycin, amphotericin B, nystatin), taxanes (e.g., paclitaxel and docetaxel), antimetabolites (e.g., 5-fluorouracil, cytarabine, premetrexed, thioguanine, floxuridine, capecitabine, gemcitabine, and methotrexate), nucleoside analogues (e.g., fludarabine, clofarabine, cladribine, penostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vincristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lumustine), enzymes (e.g., L-asparaginase), biological agents (e.g., interferons and interleukins), hexamethylmelamine, mitotane, angiogenesis inhibitors (e.g., thalidomide, lenalidomide), steroids (e.g., prednisone, dexamethasone, betulinic acid, testosterone, estrogen, progesterone, and prednisolone), hormonal agents (e.g., tamoxifen, raloxifene, leuprolide, bicalutamide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, diazepam, propofol, 2,3-mercaptopropanol, or any combination thereof. In one aspect, the anti-cancer agent is paclitaxel.

Lyoprotectant

In certain aspects, the nanodroplet compositions are lyophilized or freeze-dried to be reconstituted later. In these aspects, the nanodroplet compositions include a lyoprotectant. As used herein, a "lyoprotectant" is a molecule that protects material that has been freeze-dried or lyophilized. Examples of lyoprotectants include, but are not limited to, sugars, sugar alcohols, or other polyhydroxy compounds. Lyoprotectants useful herein can be natural or synthetic products. In further aspects, the lyoprotectant also acts as an osmoregulator.

In one aspect, the lyoprotectant is a sugar or sugar alcohol. In a further aspect, the sugar or sugar alcohol can be mannitol, sucrose, glucose, or a combination thereof. In one aspect, the lyoprotectant is mannitol.

Preparation of the Nanodroplet Compositions

In one aspect, the preparation of nanodroplets consists of two steps. In this aspect, the first step is the formation of micelles, which generally have a particle size of 20-30 nm. Further in this aspect, the second step is formation of nanodroplets from the micellar solution. Exemplary procedures for preparing the nanodroplets described herein are provided in the Examples below.

In one aspect, the formation of micelles is accomplished by mixing a copolymer having a hydrophilic block and a hydrophobic block with an anti-cancer agent as discussed above in a solvent to produce a first composition. The solvent can be organic or non-organic or a combination thereof. In one aspect, the solvent is an organic solvent including, but not limited to, acetonitrile, chloroform, dichloromethane, or any combination thereof.

Following preparation of the first composition (i.e., micelle composition), in one aspect, the solvent is removed under vacuum to produce a second composition. In one aspect, the second composition is a thin film. In another aspect, the thin film is hydrolyzed with a solution such as, for example, a buffer to produce a third composition. In some aspects, the buffer is Tris-HCl and has a pH of 8.

After preparation of the third composition, the third composition is mixed with a poloxamer and optional lyoprotectant to produce a fourth composition. Next, an oil is added to the fourth mixture to produce a fifth composition. The amount of oil used to produce the nanodroplets is important. Without wishing to be bound by theory, if the amount of oil is too low, the oil dissolves in the cores of micelles and stabilizes them. The size of nanoemulsion droplets increases with an increase in the oil/copolymer concentration ratio, and if the oil concentration is too high, drug release can be affected, as seen in experimental animal models. Thus, the optimal amount of oil will exceed the oil solubility limit in the cores of the micelles, and the oil evolves in a separate phase as a nanodroplet and a nanoemulsion stabilized with a block copolymer shell is formed around the oil core.

Following production of the fifth composition, the nanodroplets can be prepared by a technique such as, for example, homogenization with a microfluidic device. In one aspect, a higher working pressure during the homogenization step induces a smaller nanodroplet size; however, more treatment cycles with a lower working pressure can generate the same results. In some aspects, the working pressure of homogenization is from 20,000 psi to 30,000 psi. If a lyoprotectant has been added, in one aspect, the composition can be freeze-dried following nanodroplet formation. Further in this aspect, the nanodroplet composition will exist as a dry powder that can be rehydrated prior to administration to a subject.

The diameter of the nanodroplets can be measured using techniques known in the art. In one aspect, the nanodroplets have a Z-average diameter of from 100 to 200 nm as measured by dynamic light scattering (Zetasizer from Malvern Instruments; Malvern, UK). In another aspect, the nanodroplets have a Z-average diameter of from 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, or 200 nm as measured by dynamic light scattering (Zetasizer from Malvern Instruments; Malvern, UK), where any value can be a lower and upper endpoint of a range (e.g., 120 nm to 150 nm, 125 nm to 145 nm). In another aspect, the nanodroplets have a Z-average diameter of from 100 to 150 nm.

In one aspect, the dry weight ratio of the anti-cancer agent to the copolymer is from 1:4, 1:4.5, 1:5, 1:5.5, 1:6, 1:6.5, 1:7, 1:7.5, 1:8, 1:8.5, 1:9, 1:9.5, or 1:10, where any value can be a lower and upper endpoint of a range (e.g., 1:4 to 1:10, 1:5 to 1:9).

In another aspect, the dry weight ratio of the anti-cancer agent to the poloxamer is from 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10, where any value can be a lower and upper endpoint of a range (e.g., 1:1 to 1:10, 1:3 to 1:5, 1:3.5 to 1:4.5).

In another aspect, the volume percentage of the oil is from 0.2% to 2% of the final nanodroplet composition volume. In a further aspect, the volume percentage of the oil is from 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% of the final nanodroplet composition volume, where any value can be a lower and upper endpoint of a range (e.g., 0.1% to 1.5%, 0.3% to 1%). In these aspects, this volume percentage is the feeding volume percentage of oil as it relates to the volume of an aqueous solution containing the nanodroplets. In another aspect, the weight ratio of oil to the copolymer is from 0.1 to 1, or is from 0.1 to 0.5, or is from 0.15 to 0.3.

In another aspect, when a lyoprotectant is used, the amount of lyoprotectant is from 1% to 10% (w/w) of lyoprotectant to the weight of the final aqueous solution of nanodroplets before lyophilization. In another aspect, the amount of lyoprotectant is 1%, 2%, 3%, 4%, 5%, 6%, 7%, 8%, 9%, or 10% (w/w) of lyoprotectant to the weight of the final aqueous solution of nanodroplets before lyophilization, where any value can be a lower and upper endpoint of a range (e.g., 2% to 8%, 4% to 6%). In another aspect, the dry weight ratio of the lyoprotectant to the copolymer is from 0.1 to 1, or is from 0.1 to 0.6, or is from 0.2 to 0.6, or is 0.1, 0.2, 0.3, 0.4, 0.5, or 0.6.

In one aspect, the nanodroplets are an aqueous emulsion that include the following components:
(a) a copolymer with a hydrophilic block consisting of monomethoxy polyethylene glycol (mPEG) having a molecular weight from 1,500 Da to 2,500 Da and a hydrophobic block consisting of poly(D,L)-lactide having a molecular weight of from 1,500 to 2,500 Da;
(b) a poloxamer with the formula $HO(C_2H_4O)_b(C_3H_6O)_a(C_2H_4O)_bH$
wherein a is from 25 to 35 and b is from 70 to 80;
(c) an oil that is a mixture of caprylic triglyceride and capric triglyceride;
(d) an anti-cancer agent; and
(e) a lyoprotectant, wherein the lyoprotectant is mannitol.

In another aspect, the nanodroplets are an aqueous emulsion that include the following components:
(a) a copolymer with a hydrophilic block consisting of monomethoxy polyethylene glycol (mPEG) having a molecular weight from 1,500 Da to 2,500 Da and a hydrophobic block consisting of poly(D,L)-lactide having a molecular weight of from 1,500 to 2,500 Da;
(b) a poloxamer with the formula $HO(C_2H_4O)_b(C_3H_6O)_a(C_2H_4O)_bH$
wherein a is from 25 to 35 and b is from 70 to 80;
(c) an oil that is a mixture of caprylic triglyceride and capric triglyceride;
(d) paclitaxel; and
(e) a lyoprotectant, wherein the lyoprotectant is mannitol, where (i) the dry weight ratio of paclitaxel to the copolymer is from 1:5 to 1:9, and (ii) the dry weight ratio of paclitaxel to the poloxamer is from 1:3 to 1:5.

In another aspect, the nanodroplets are an aqueous emulsion that include the following components:
(a) a copolymer with a hydrophilic block consisting of monomethoxy polyethylene glycol (mPEG) having a molecular weight from 1,500 Da to 2,500 Da and a hydrophobic block consisting of poly(D,L)-lactide having a molecular weight of from 1,500 to 2,500 Da;
(b) a poloxamer with the formula $HO(C_2H_4O)_b(C_3H_6O)_a(C_2H_4O)_bH$
wherein a is from 25 to 35 and b is from 70 to 80;
(c) an oil that is a mixture of caprylic triglyceride and capric triglyceride;
(d) paclitaxel; and
(e) a lyoprotectant, wherein the lyoprotectant is mannitol, where (i) the dry weight ratio of paclitaxel to the copolymer is from 1:5 to 1:9, (ii) the dry weight ratio of paclitaxel to the poloxamer is from 1:3 to 1:5, (iii) the oil is from 0.2% to 2% by volume percent of the final nanodroplet composition volume, and (iv) the lyoprotectant is from 1% to 10% (w/w) of the final aqueous solution of nanodroplets before lyophilization.

In any of the previous aspects, the oil can additionally include PFOB in a ratio of PFOB to other oil components (w/w) from 1 to 5 or from 2 to 4.

In any of the previous aspects, the nanodroplets have a Z-average diameter of from 125 nm to 150 nm, 125 nm to 145 nm, 130 nm to 150 nm, 135 nm to 150 nm, 130 nm to 145 nm, or 130 nm to 140 nm as measured by dynamic light scattering (Zetasizer from Malvern Instruments; Malvern, UK).

Additional Components

In other aspects, additional components can be added to the nanodroplets described herein in order to enhance the anti-cancer properties of the nanodroplets. In one aspect, any of the nanodroplets described herein include one or more anti-body drug conjugates (ADCs). ADCs are used in oncology applications to assist in the local delivery of cytotoxic or cytostatic agents and the targeted delivery of the drug moiety to tumors, which can allow higher efficacy, lower toxicity.

In one aspect, the ADC is a maytansinoid. Maytansinoid compounds suitable for use herein are well known in the art, and can be isolated from natural sources according to known methods, produced using genetic engineering techniques (see Yu et al (2002) PNAS 99:7968-7973), or maytansinol and maytansinol analogues prepared synthetically according to known methods. In one aspect, the maytansinoid compound is DM1 (disclosed in U.S. Pat. No. 5,208,020, incorporated by reference) and DM4 (disclosed in U.S. Pat. No. 7,276,497, incorporated by reference). In another aspect, the ADC is a dolastatin or auristatin.

Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anti-cancer (U.S. Pat. No. 5,663,149) and antifungal activity (Pettit et al (1998) Antimicrob. Agents Chemother. 42:2961-2965). Examples of auristatins useful herein include MMAE (see U.S. Pat. No. 6,884,869), MMAF (US 2005/0238649, U.S. Pat. Nos. 5,767,237 and 6,124,431), auristatin F (AF), and auristatin PE. An example of a dolastatin useful herein includes dolastatin 10.

In another aspect, the ADC can be a calicheamicin. The calicheamicins are a class of enediyne antitumor antibiotics derived from the bacterium *Micromonospora echinospora*, with calicheamicin γ1 being the most notable. Mylotarg® is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference.

In another aspect, the ADC is a duocarmycin. Examples of duocarmycins useful herein include duocarmycin A (U.S. Pat. No. 4,923,990, incorporated by reference) and duocarmycin SA (U.S. Pat. No. 5,101,038, incorporated by reference), as well as large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/089149, WO2009/017394A1, U.S. Pat. Nos. 5,703,080, 6,989,452, 7,087,600, 7,129,261, 7,498,302, and 7,507,420.

In another aspect, any of the nanodroplets described herein include one or more p-glycoprotein inhibitors. Not wishing to be bound by theory, the p-glycoprotein inhibitor can enhance the intracellular accumulation of anti-cancer agent impairing the p-glycoprotein. In one aspect, the p-glycoprotein inhibitor is verapamil, cyclosporin, tamoxifen, calmodulin antagonists, dexverapamil, dexniguldipine, valspodar (PSC 833), biricodar (VX-710), tariquidar (XR9576), zosuquidar (LY335979), laniquidar (R101933), elacridar (GF120918), timcodar (VX-853), taxifolin, naringenin, diosmin, quercetin, diltiazem, bepridil, nicardipine, nifedipine, felodipine, isradipine, trifluorperazine, clopenthixol, trifluopromazine, flupenthixol, emopamil, gallopamil, Ro1 1-2933, or any combination thereof.

In another aspect, the p-glycoprotein inhibitor is tariquidar. Tariquidar is an anthranilamide derivative with multi-drug resistance properties. Not wishing to be bound by theory, tariquidar can non-competitively bind to the p-glycoprotein transporter, thereby inhibiting transmembrane transport of anti-cancer drug. Inhibition of transmembrane transport may result in increased intracellular concentrations of an anti-cancer agent, which ultimately enhances its cytotoxicity. In one aspect, the weight ratio of tariquidar to the copolymer (e.g., mPEG-PDLLA) is from 0.001 to 0.015. In another aspect, the weight ratio of tariquidar to the copolymer (e.g., mPEG-PDLLA) is 0.001, 0.002, 0.003, 0.004, 0.005, 0.006, 0.007, 0.008, 0.009, 0.010, 0.011, 0.012, 0.013, 0.014, or 0.015, where any value can be a lower or upper end-point of a range (e.g., 0.005 to 0.015, 0.07 to 0.012, etc.).

In another aspect, any of the nanodroplets described herein include one or more perfluoro compounds. In one aspect, the perfluoro compound is a fluoro ether. The term "fluoro ether" as used herein is any organic ether possessing at least one fluoro group. Depending upon the application, the fluoro ether can contain multiple fluoro groups. For example, all of the hydrogen atoms of the organic ether can be substituted with a fluoro group. In one aspect, the fluoro ether described herein includes a linear fluoro ether having the following I:

$$R^1-(X^1-O-X^2)_n-R^2 \qquad I$$

wherein $X^1$ and $X^2$ are, independently, $(CF_2)_y$, $(CHF)_y$, or $(CF_2-CHF)_y$;
$R^1$ and $R^2$ are, independently hydrogen, an alkyl group, an aryl group, an alkoxy group, a hydroxyl group, or a halogenated group, wherein one or both of $R^1$ and $R^2$ are optionally fluorinated;
O is oxygen;
y is 1, 2, 3, 4, 5, 6, 7, 8, 9, 10, 11, 12, 13, 14, 15, 16, 17, 18, 19, or 20; and
n is 1, 2, 3, 4, 5, 6, 7, 8, 9, 10, 11, 12, 13, 14, 15, 16, 17, 18, 19, or 20,
wherein the fluoro ether has at least 16 fluorine atoms.

For imaging purposes, with respect to the fluorine atoms, the fluoro ether should be symmetrical. For example, referring to formula I above, $X^1$ and $X^2$ are the same fluoro groups. In certain aspects, $R^1$ and $R^2$ are also identical. When the fluoro groups are symmetrical, the $^{19}$F MR spectrum is not broad and, thus, useful in imaging the nanoemulsion. The number of fluorine atoms present in the fluoro ether can also determine the intensity of the signal in the $^{19}$F MR spectrum. The fluoro ether has at least 16 fluorine atoms, at least 18 fluorine atoms, or at least 20 fluorine atoms. In one aspect, the linear fluoro ether has the formula $R^1O-[CF_2-CF_2-O-]_n-R^2$, where n is at least 5 and $R^1$ and $R^2$ do not contain fluorine. In other aspects, the fluoro ether can be oligomers or polymers. For example, referring to formula I, n can be greater than 20.

In one aspect, the fluoro ether is a perfluoro crown ether, or a combination thereof. Crown ethers are heterocyclic chemical compounds that are composed of a ring containing several ether groups. The most common crown ethers are oligomers of ethylene oxide the repeating unit being ethyleneoxy, i.e., —CH$_2$CH$_2$O—. However, other alkylene oxides can be present in the crown ether including, but not limited to, propylene oxide, butylene oxide, and the like. Examples of this series of compounds are the tetramer (n=4), the pentamer (n=5), the hexamer (n=6), the heptamer (n=7), the octamer (n=8), the decamer (n=10), and the like. Similar to the linear fluoro ethers described above, the perfluoro crown ether has at least 16 symmetrical fluorine atoms. In other aspects, perfluoro crown ether is any crown ether with all hydrogen atoms substituted with fluorine atoms. Examples of perfluoro crown ethers include, but are not limited to, perfluoro 12-crown-4 ether, perfluoro 15-crown-5 ether, perfluoro 18-crown-6 ether, perfluoro 21-crown-7 ether, perfluoro dibenzo-18-crown-6 ether, perfluoro diaza-18-crown-6 ether, or any combination thereof. In one aspect, In one aspect, the amount of perfluoro crown ether is from 100 µL to 1 mL per 1 g of the copolymer (e.g., mPEG-PDLLA). In another aspect, the amount of perfluoro crown ether is 100 µL, 200 µL, 300 µL, 400 µL, 500 µL, 600 µL, 700 µL, 800 µL, 900 µL, or 1 mL per 1 g of the copolymer, where any value can be a lower or upper end-point of a range (e.g., 100 µL to 500 µL, 200 µL to 400 µL etc.).

In another aspect, the perfluoro compound can be a perfluoroalkyl, a perfluorocycloalkyl, a perfluoroalkylene, or a perfluoroalkynes. Examples of perfluoroalkyl compounds and examples of perfluorocycloalkyl compounds include, but are not limited to, perfluoromethane, perfluoroethane, perfluoropropane, perfluorocyclopropane, perfluorobutane, perfluorocyclobutane, perfluoropentane, perfluorocyclopentane, perfluorohexane, perfluorohexane, perfluoroheptane, perfluorocycloheptane, perfluorooctane, perfluorocyclooctane, perfluorononane, and perfluorodecane.

The imaging of the tumor with the nanodroplets containing the perfluoro compound aids in the application of the ultrasound to the tumor. By identifying the precise location of the nanodroplets in the tumor, it is possible to apply a focused beam of ultrasound energy to the tumor in order to convert the nanodroplets into microbubbles and subsequently release the anti-cancer agent in the tumor. For example, using $^{19}$F MRI can pinpoint the location of the nanodroplets. This approach ultimately results in a much more efficient and effective way to deliver the anti-cancer agent to tumors.

Any of the components above can be added subsequent to the formation of the nanodroplets described herein. In the alternative, the additional components can be added to one or more components used to produce the nanodroplets.

Pharmaceutical Compositions

Any of the nanodroplet compositions described herein can be combined with at least one pharmaceutically-acceptable carrier to produce a pharmaceutical composition suitable for administration to a subject. The pharmaceutical compositions can be prepared using techniques known in the art. In one aspect, the pharmaceutical composition is prepared by admixing the nanodroplets with a pharmaceutically-acceptable carrier.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in pharmaceutical compositions. Pharmaceutical compositions may include carriers, thickeners, diluents, buffers, preservatives, surface active agents, and the like, in addition to the molecule or nanodroplet composition of choice. Pharmaceutical compositions can also include one or more additional active ingredients such as antimicrobial agents, anti-inflammatory agents, anesthetics, and the like.

In some aspects, the nanodroplet compositions described herein are provided as a dry (lyophilized) powder and can be reconstituted in water or another appropriate vehicle for intravenous administration as described below.

Excipients

The compositions described herein can be formulated in any subject the patient or entity can tolerate to produce pharmaceutical compositions. Examples of such excipients include, but are not limited to, water, aqueous hyaluronic acid, saline, Ringer's solution, dextrose solution, Hank's solution and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, cresols, formalin, and benzyl alcohol. In certain aspects, the pH can be modified depending upon the mode of administration. Additionally, the compositions can include carriers, thickeners, diluents, preservatives, surface active agents (surfactants), and the like, in addition to the compounds described herein.

Method of Administration

The pharmaceutical compositions can be administered in a number of ways depending on whether local or systemic treatment is desired, and on the area to be treated. Administration can be parenterally, orally, subcutaneously, intralesionally, intraperitoneally, intravenously, or intramuscularly. In one aspect, the preferred mode of administration is intravenous injection. In other aspects, if a tumor is present in the subject, the nanodroplet composition can be administered directly at or in the tumor via injection.

Cancer Treatment

In some aspects, the compositions described herein are applicable for treating a variety of different types of cancers. In one aspect, the cancer includes prostate cancer, leukemia (e.g., acute myologenous leukemia, acute promyelocytic leukemia, acute lymphoblastic leukemia, chronic myelogenous leukemia, chronic lymphocytic leukemia, hairy cell leukemia, plasma cell leukemia), myeloproliferative disorders (e.g., essential thrombocytosis, polythemia vera, primary myelofibrosis), myelodysplastic syndromes, lymphoma (Hodgkin and non-Hodgkin), testicular cancer, head and neck cancer, esophageal cancer, stomach cancer, liver cancer, cancer of the small intestine, gall bladder cancer, rectal or anal cancer, sarcomas, uterine or cervical cancer, bladder cancer, bone cancer, renal cancer, melanoma and other skin cancers, colon cancer, ovarian cancer, lung cancer, cancers of the central nervous system, multiple myeloma, or breast cancers.

In one aspect, a method for treating cancer in a subject is provided. In this aspect, the nanodroplet compositions are administered to a subject. In a further aspect, the nanodroplets are administered to the subject by intravenous injection.

In a still further aspect, the subject receiving the nanodroplet compositions has been diagnosed with pancreatic cancer, lung cancer, breast cancer, ovarian cancer, prostate cancer, or colon cancer. In one aspect, a cancerous tumor in a subject will be reduced in size upon administration of the nanodroplet compositions.

In one aspect, the dosage of the anti-cancer agent administered to the subject in the form of the nanodroplet compositions is from 30 mg/kg of body weight to 50 mg/kg of body weight per single administration or is about 40 mg/kg of body weight. In a further aspect, the nanodroplets are administered to the subject at least once a week, at least two times per week, or at least three times per week. In one aspect, optimal results are achieved with intravenous injection of the nanodroplet compositions at a dosage of 40 mg/kg of body weight twice per week for two weeks. Without wishing to be bound by theory, this dosage level provides a balance between a higher dosage of anti-cancer agent and acceptable side effects and/or lower toxicity.

As discussed in more detail in the Examples, the nanodroplet formulations described herein are more stable than commercial micellar or nanoparticle products incorporating paclitaxel but lacking an added oil such as, for example, a synthetic mimetic of GENEXOL® PM. In one aspect, the present nanodroplet formulations are at least 2 times, at least 3 times, at least 4 times, or at least 5 times more stable than formulations that do not incorporate the oil. Direct comparisons will be provided in the Examples.

In another aspect, the nanodroplet formulations described herein are more effective at treating cancers and/or tumors in subjects than commercial micellar or nanoparticle products that incorporate paclitaxel but lack an added oil. In one aspect, the present nanodroplet formulations are at least 2 times, at least 3 times, at least 4 times, or at least 5 times more effective than formulations that do not incorporate the oil. In another aspect, the nanodroplet formations are more effective at treating cancers and/or tumors in subjects than commercial protein-bound anti-cancer agents such as, for example, ABRAXANE® (Celgene Corporation, Summit, N.J.). Direct comparisons will be provided in the Examples.

In a further aspect, the nanodroplet formulations release their paclitaxel more slowly when compared to commercial products. Without wishing to be bound by theory, this slower release allows for larger doses of paclitaxel to be given with lower toxicity and fewer systemic side effects than formulations currently on the market. Direct comparisons will be provided in the Examples.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

Example 1

Preparation of the Nanodroplets

Components

A sample nanodroplet composition was produced using paclitaxel as the anti-cancer agent, an mPEG-PDLLA copolymer, PLURONIC® P188 as the poloxamer, mannitol as lyoprotectant, a Tris-HCl buffer, and MIGLYOL® 812 as the oil.

The copolymer was generated by melt polymerization and solvent polymerization and the preferred molecular weights of the blocks were 2,000 Daltons for mPEG and 2,000 Daltons for PDLLA.

Micelle Formation

Micelles were generated according to the following procedure.
1. Paclitaxel and mPEG-PDLLA were dissolved in acetonitrile.
2. Solvents were removed under vacuum with heating.
3. The thin film resulting from solvent evaporation was hydrolyzed with a solution of Tris-HCl buffer to generate micelles.
4. PLURONIC® P188 and lyoprotectant mannitol were dissolved in the aqueous micellar solution.
5. MIGLYOL® 812 was added to the aqueous micellar solution.
Nanodroplet Formation To form nanodroplets from the micellar solution, the following additional steps were performed:
6. The pre-mixture was gently agitated.
7. The agitated pre-mixture was homogenized under high pressure in a microfluidic device.

The composition produced above is a non-limiting example of a nanodroplet composition; however, multiple parameters can be varied to generate functional compositions.

Molecular Weight of Copolymer and Polymer Synthesis

Molecular weights of mPEG-PDLLA ranging from 1,540 to 2,200 Daltons for the PDLLA part and 2000 Daltons for the mPEG part were used to generate nanodroplet compositions.

Solvent Parameters

Solvents tested included acetonitrile, chloroform, dichloromethane, and other organic solvents. The ideal solvent was determined to be able to dissolve both the anti-cancer agent and the copolymer. Additionally, the boiling point of the ideal solvent was found to less than 100° C. In one instance, removal of acetonitrile under vacuum was accomplished at 60° C.

Buffer pH and Concentration

A Tris-HCl buffer was used to vary the pH of the solution. Tris-HCl is a suitable buffer from about pH 7 to about pH 9. Several pH values were evaluated and the best results were obtained at pH 8. Concentrations of Tris-HCl ranged from 0.05 M to 0.5 M, with the preferred results obtained at a concentration of 0.1 M.

Hydrolysis of the thin film in the third step above was accomplished both at room temperature and under gentle heating, with the best hydrolysis results occurring at a temperature of 60° C.

It was also found that the volume of Tris-HCl buffer added to the formulations was able to control the concentration of the micelle solution. Optimal results were obtained when paclitaxel was present at a concentration of 5 mg/mL.

Poloxamer Identity

Various poloxamers were evaluated for their abilities to aid in nanodroplet formation and uptake of anti-cancer agent into nanodroplet compositions. Among these were PLURONIC® P188 and PLURONIC® P407, with PLURONIC® P188 exhibiting more desirable results.

Weight Ratio of Anti-Cancer Agent to Poloxamer

Multiple weight ratios of the anti-cancer agent paclitaxel to the poloxamer PLURONIC® P188 were tested. Ratios ranged from 1:1 to 1:10, with optimal results at a weight ratio of 1:4.

Lyoprotectant Concentration

Various concentrations of the lyoprotectant mannitol were evaluated. The final concentration of mannitol in aqueous solution ranged from 1% to 10% (w/w) with optimal results observed at 1% to 5% (w/w).

Oil Identity and Volume

Various oils were evaluated. These included MIGLYOL® 810, 812, 818, 829, and 840. MIGLYOL® 812 was further tested in different amounts ranging from 0.2% (v/v) to 2% (v/v), with best results in the range of 0.3% (v/v) to 1% (v/v). Additionally, PFOB was used as the oil or as a component of the oil in some formulations.

Agitation of Mixture

The final mixture was agitated at speeds of from 3,000 rpm to 6,000 rpm for times of from 1 minute to 3 minutes.

High Pressure Homogenization

The working pressure for homogenization ranged from 20,000 psi to 30,000 psi. Homogenization cycles were generally repeated 2 or 3 times.

Preferred Compositions

Table 1 below presents preferred amounts of the components discussed above for nanodroplet compositions.

TABLE 1

Preferred Nanodroplet Compositions

| Component | Amount per mL |
| --- | --- |
| Paclitaxel | 2-5 mg |
| mPEG-PDLLA | 10-45 mg |
| P188 | 6-25 mg |
| MIGLYOL ® 812 | 1.5-13.5 mg |
| Mannitol | 2-27 mg |
| PFOB (optional) | 3-54 mg |
| Water for injection | q.s. |

Characterization of Nanodroplets

Figure 2:
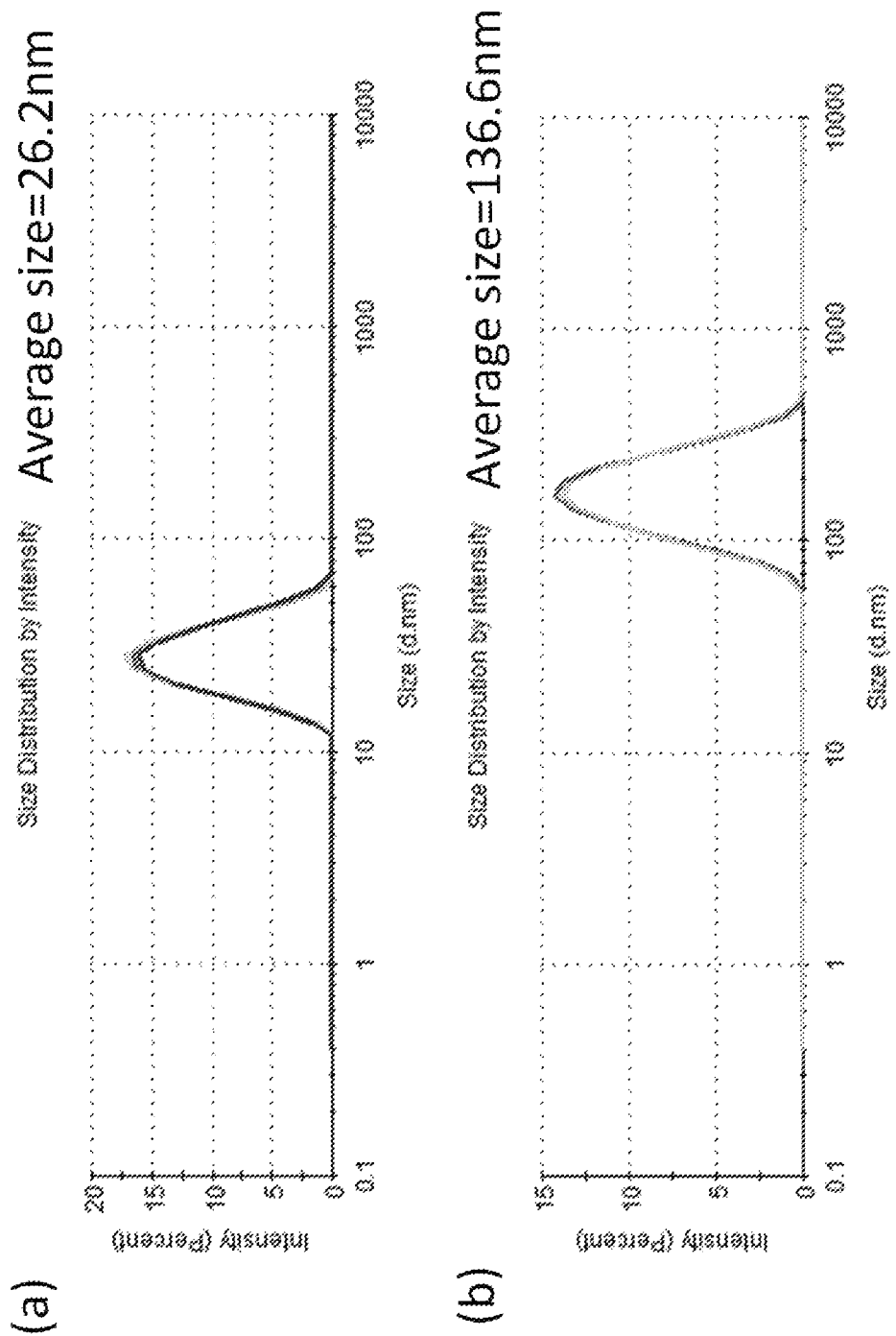
FIG. 2 shows dynamic light scattering results evaluating particle size before (a) and after (b) the addition of an oil to the formulations disclosed herein. As seen in this figure, the Z-average diameter increases with the addition of oil to a micellar solution to form nanodroplets.

Micelles and nanodroplets were characterized by dynamic light scattering (Zetasizer from Malvern Instruments, Malvern, UK). Micelles typically had Z-average diameters of 20-30 nm before the nanodroplet formation step (see step 7 in Example 1), while nanodroplets had Z-average diameters ranging from 100 to 150 nm (FIG. 1 and FIG. 2). Z-average diameter increased with increasing oil concentration.

Efficacy of Nanodroplets

Timed Release

Figure 3:
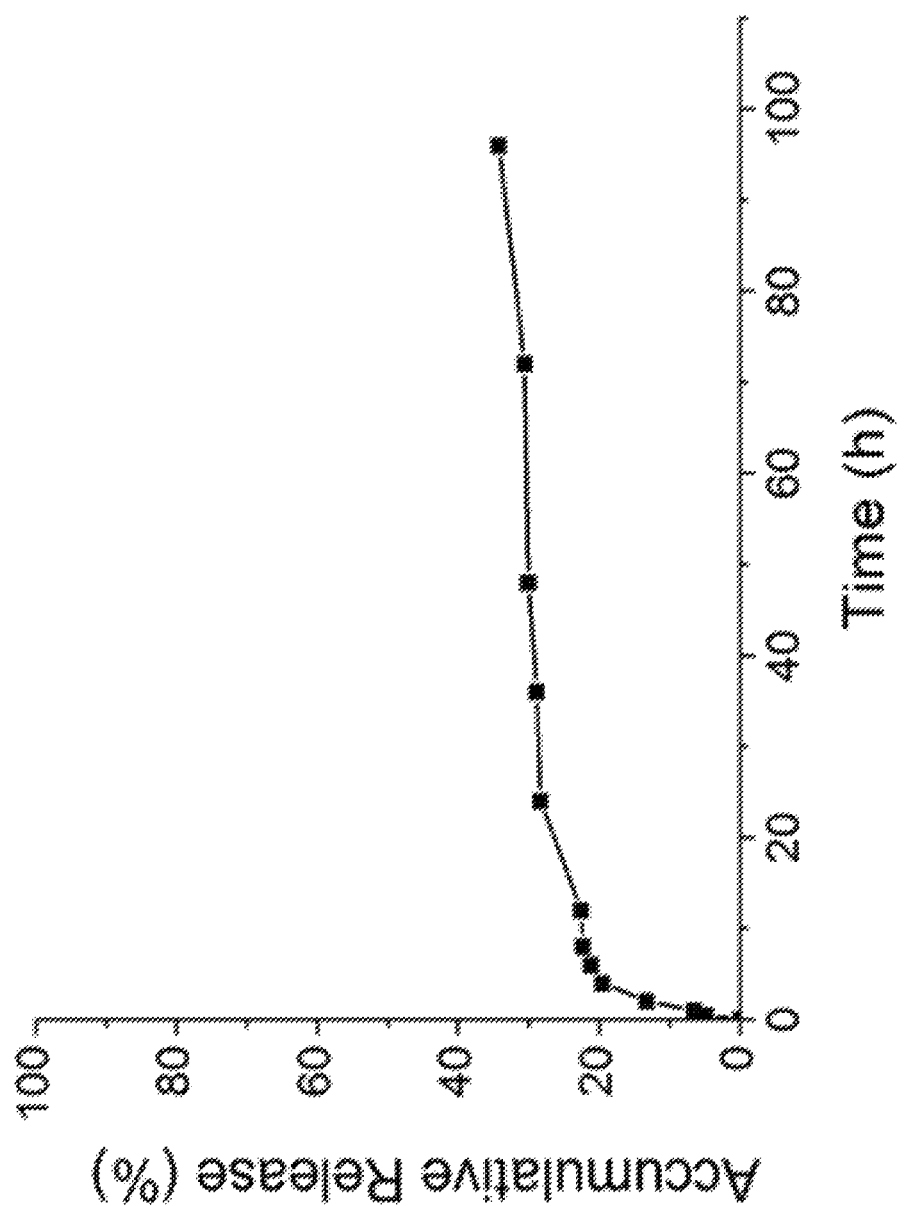
FIG. 3 shows the release of paclitaxel over time from the nanodroplets disclosed herein; the nanodroplets provide a much more stable sustained release than currently available commercial products.

Release of paclitaxel over time was evaluated for the present nanodroplet formulations. The nanodroplet formulations had a slow release profile (FIG. 3), with only about 40% of the paclitaxel released after 100 hours. Thus, the nanodroplet formulations can successfully protect against premature release of the drug.

Toxicity

Figure 4:
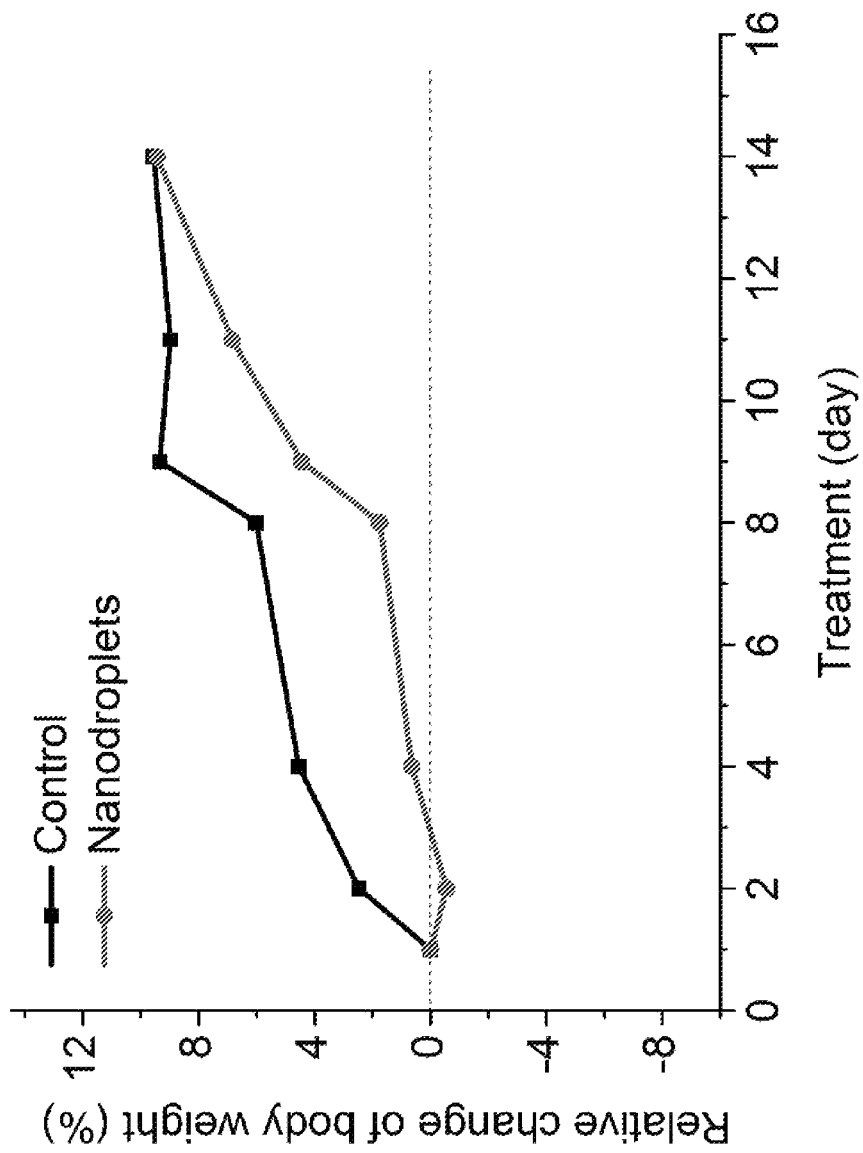
FIG. 4 shows the effect of the nanodroplets on relative body weight for nude mice without tumors. Groups of mice (n=5) were injected through the tail vein twice per week for two weeks with the dose of paclitaxel being fixed at 0.8 mg/animal per injection. At the end of the trial, mice in the nanodroplet treatment group did not have a significantly different body weight from control mice.

In addition to the slower release time for paclitaxel from the nanodroplet formulations, toxicity and/or systemic effects as estimated by change in body weight were assessed for nanodroplet-treated mice versus a control. Nude mice without tumors were injected through the tail vein a total of four times over two weeks with a dose of 0.8 mg per animal per injection. At the end of the trial, mice in the nanodroplet treatment group did not experience a significant change in body weight compared to untreated mice (FIG. 4). As seen below, this lack of toxicity is compatible with anti-tumor growth efficacy of the nanodroplet compositions.

Micelles Versus Nanodroplets—In Vivo Studies

Figure 5:
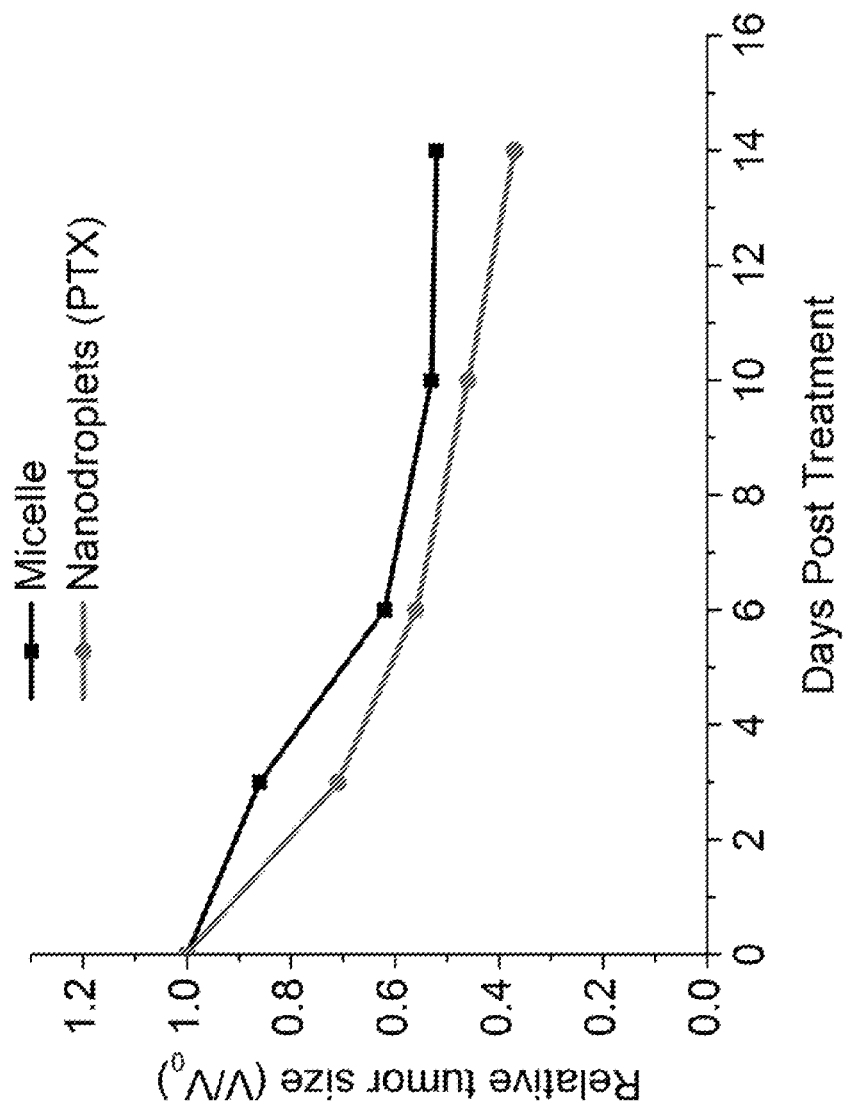
FIG. 5 shows the relative tumor volume change (pancreatic cancer cell line MIA PaCa-2) for the MIGLYOL® 812 nanodroplet (PTX) versus the mimetic GENEXOL® PM (micelle). Initial tumor volume for both groups was about 200 $mm^3$ after injection through the tail vein with a dose of 0.7 mg paclitaxel per animal twice per week for total of four injections. The relative tumor size decreased to about 0.52 for the micelle group and to about 0.44 for the nanodroplet group, showing the nanodroplet formulation to be more effective at decreasing tumors than micelles.
Figure 6:
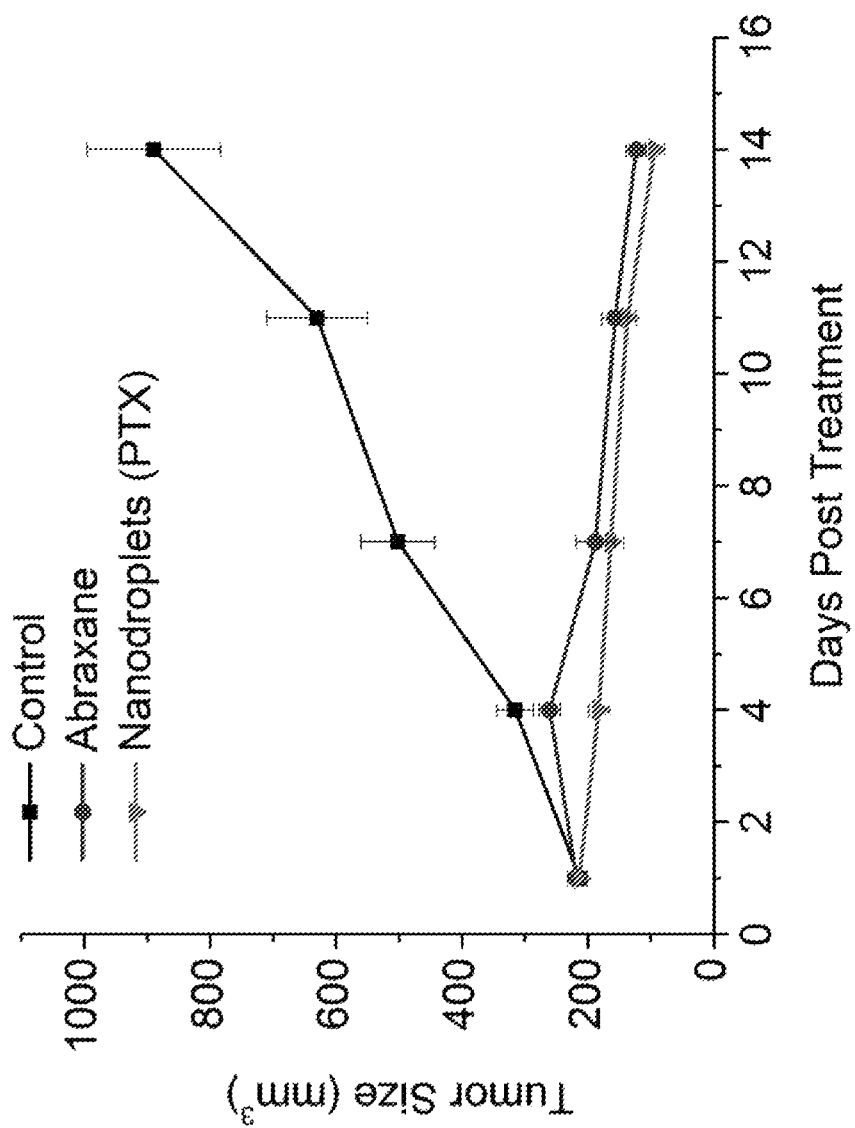
FIG. 6 shows decrease in tumor volume (pancreatic cancer cell line MIA PaCa-2) after treatment with ABRAXANE® versus a PTX nanodroplet composition, wherein the oil in the nanodroplet composition was MIGLYOL® 812. Initial tumor volume for both groups was about 200 $mm^3$ after injection through the tail vein with a dose of 0.7 mg paclitaxel per animal twice per week for total of four injections. The relative tumor size decreased to about 0.56 for the ABRAXANE® group and to about 0.44 for the nanodroplet group, showing the nanodroplet formulation to be more effective at decreasing tumors than ABRAXANE®.

A micellar solution was prepared that is equivalent synthetic mimetic of GENEXOL® PM. Mice were induced with pancreatic tumors (MIA PaCa-2). When the tumor volume reached 200 mm³, groups of tumor-bearing mice were injected a total of four times (two injections per week) with a dose of 35 mg/kg paclitaxel via either the micellar solution or a nanodroplet composition. Tumor size shrank in both groups but tumor size was smaller in the nanodroplet group than in the micelle group (FIGS. 5 and 6).

Extravasation was also faster for micelles, which could result in concentration gradient-induced particle flow from tumor tissue to normal organs until particle concentration is equilibrated over all accessible tissue, resulting in decreased tumor targeting efficiency.

Figures 7A, 7B:
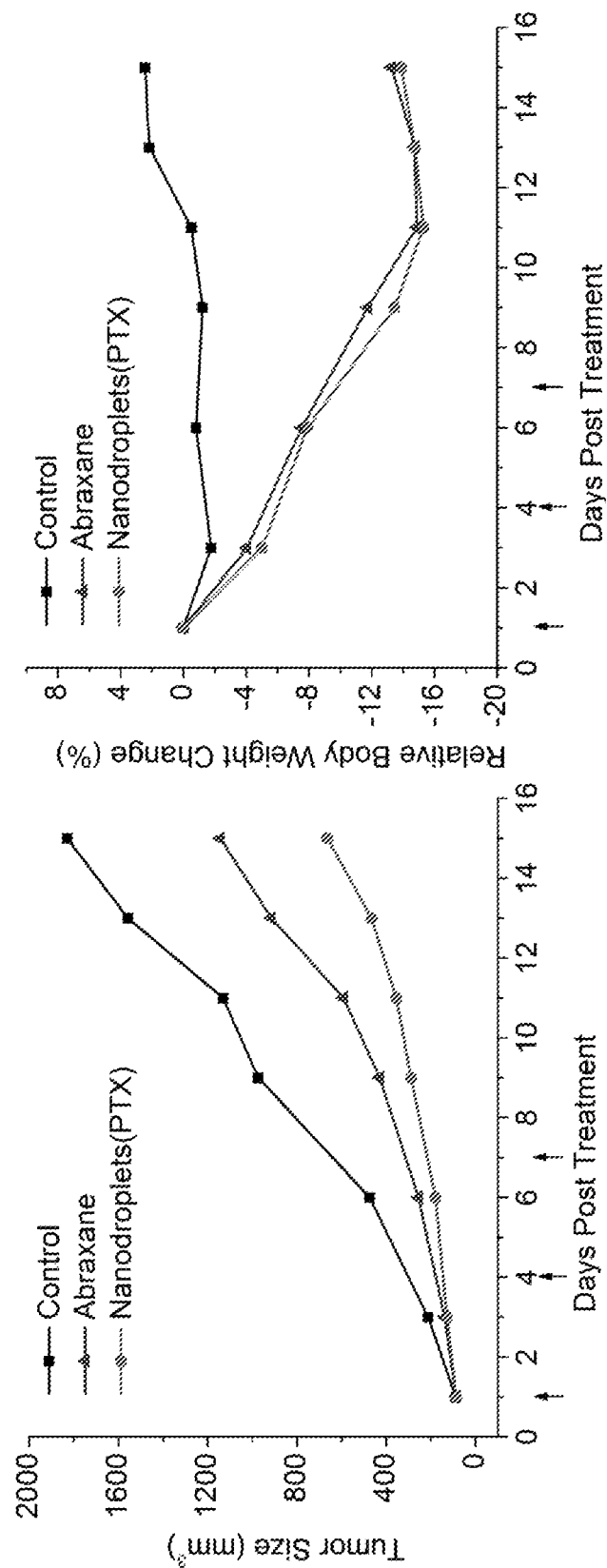
FIGS. 7A and 7B show the tumor growth inhibition efficiency (lung cancer cell line H460) of the nanodroplet (PTX) treatment versus ABRAXANE®, a peptide-bound paclitaxel formulation, wherein the oil in the nanodroplet composition was MIGLYOL® 812.

In a second study, lung cancer cell H460 suspensions were injected subcutaneously on the backs of mice to establish the tumor model. When tumor volume reached approximately 90 mm³, groups of tumor-bearing mice (n=5) were injected through the tail vein with a dose of 0.7 mg paclitaxel per animal every three days for total of three injections. At the end of two weeks, tumor size was smaller in the nanodroplet group (MIGLYOL® 812 and PFOB as oil component) than in the ABRAXANE® group (FIG. 7A). Tumor growth inhibition (TGI), which was calculated according to the following equation: TGI (%)=(1−(TVTreatment/Dn−TVTreatment/D1)/(TVControl/Dn−TVControl/D1))×100% for nanodroplets was 66.8% compared with 39.3% for ABRAXANE® group, and the body weight loss was similar for two treatment groups (FIG. 7B).

Figures 8A, 8B:
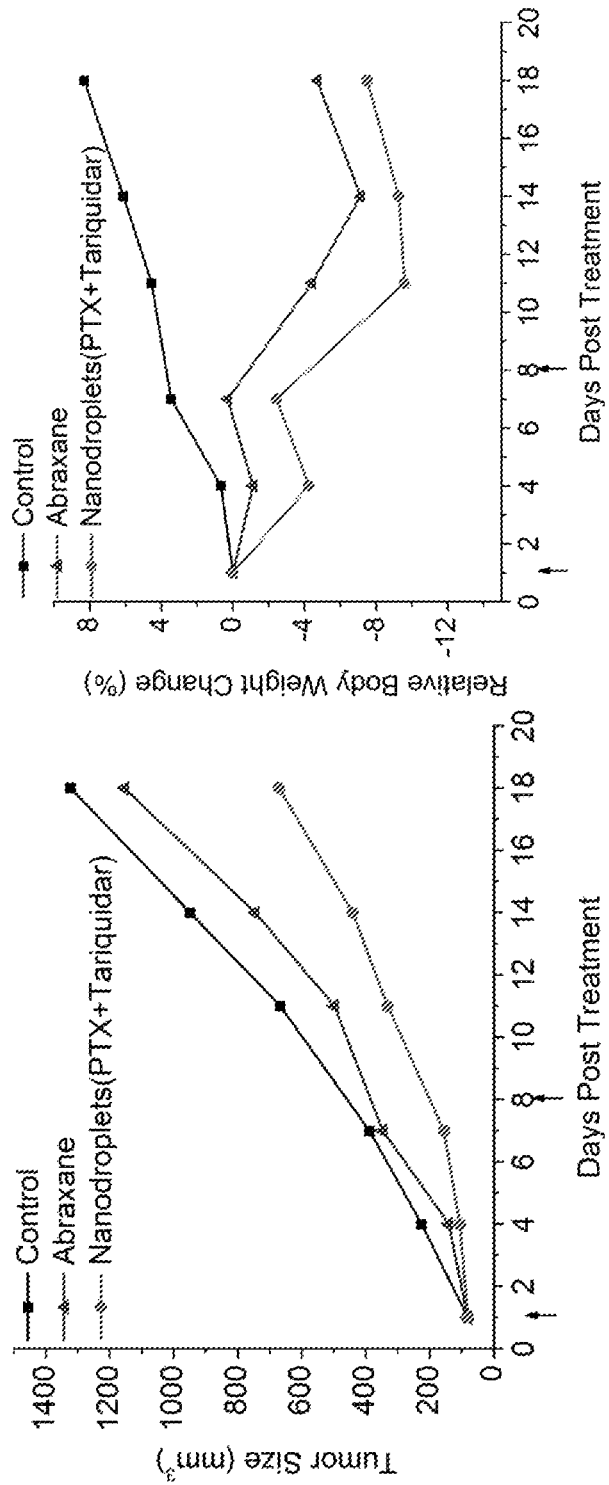
FIGS. 8A and 8B show the tumor growth inhibition efficiency of the nanodroplet (PTX+tariquidar) treatment versus ABRAXANE®, a peptide-bound paclitaxel formulation, wherein the oil in the nanodroplet composition was MIGLYOL® 812.

In a third study, lung cancer cell H460 suspensions were injected subcutaneously on the backs of mice to establish the tumor model. When tumor volume reached approximately 80 mm³, groups of tumor-bearing mice (n=5) were injected through the tail vein with a dose of 0.7 mg paclitaxel per animal every week for total of two injections for ABRAXANE® group compared with 0.6 mg paclitaxel per animal every week for total of two injections for nanodroplets (PTX+tariquidar) group. At the end of two weeks, tumor size was smaller in the nanodroplet group (even with a lower dose) than in the ABRAXANE® group (FIG. 8A). Tumor growth inhibition (TGI), which was calculated according to the following equation: TGI (%)=(1−(TVTreatment/Dn−TVTreatment/D1)/(TVControl/Dn−TVControl/D1))×100% for nanodroplets was 58.5% compared with 23.4% for ABRAXANE® group. In this case, the weight ratio of tariquidar to the copolymer (mPEG-PDLLA) is 0.01. The nanodroplet (PTX+tariquidar) treated mice group body weight loss was slightly more than ABRAXANE group initially, however both groups body weight loss were in acceptable range and with soon recovery (FIG. 8B).

Oil Variation

Figure 12:
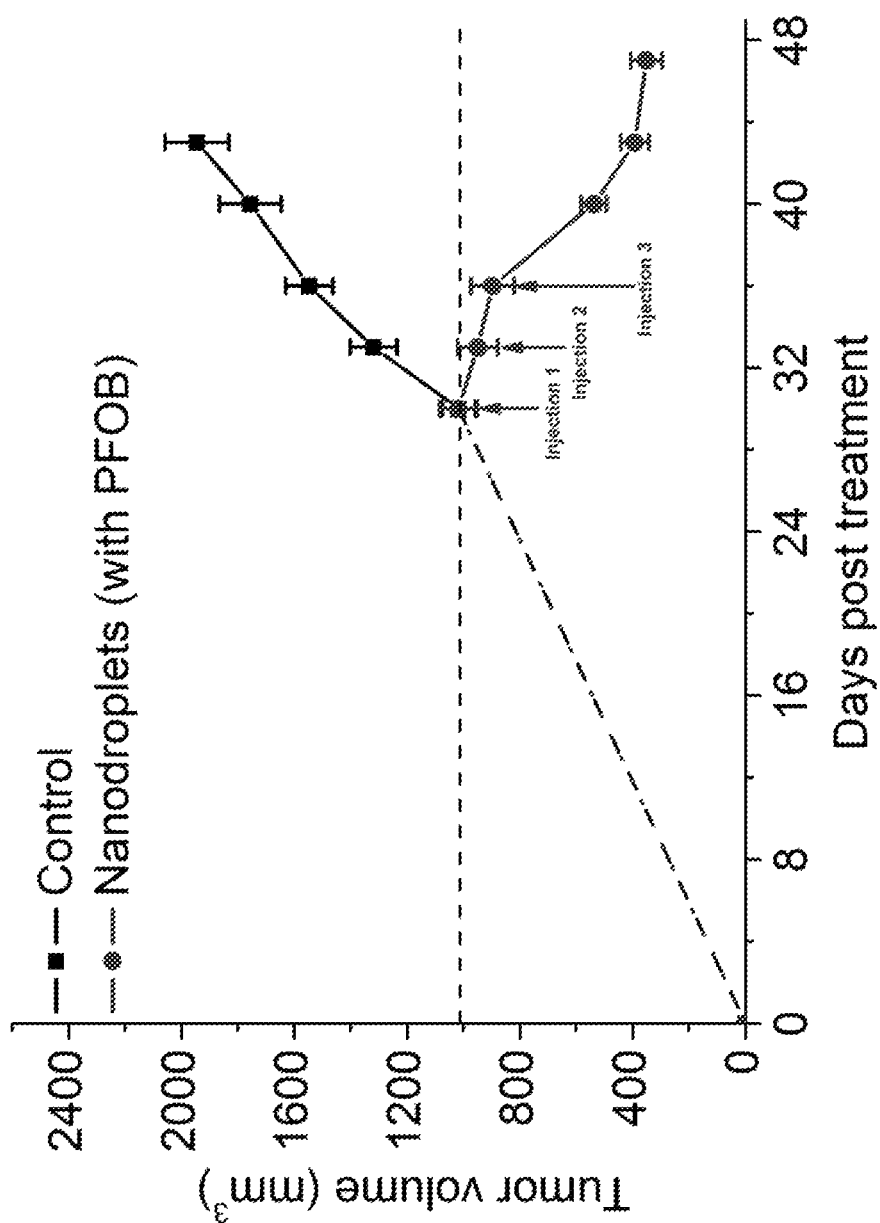
FIG. 12 shows tumor growth inhibition efficiency of nanodroplet treatment. MIA PaCa-2 cell suspensions were injected subcutaneously on the backs of mice to establish the tumor model. When tumor volume reached approximately 1000 mm$^3$, groups of tumor-bearing mice (n=5) were injected through the tail vein twice per week (a total of three times) with a dose of 0.8 mg paclitaxel (via nanodroplet formulation) per animal. Tumor size shrank in treated mice and grew in untreated controls. The oil composition in the nanodroplets was MIGLYOL® 812 and PFOB.

The oil in the nanodroplet compositions was varied including preparing formulations having the oil MIGLYOL® 812 and formulations having combined MIGLYOL® 812 and PFOB as the oil. Three injections with nanodroplets prepared with either component resulted in a significant decrease in tumor volume compared to untreated controls (FIG. 12).

Figure 9:
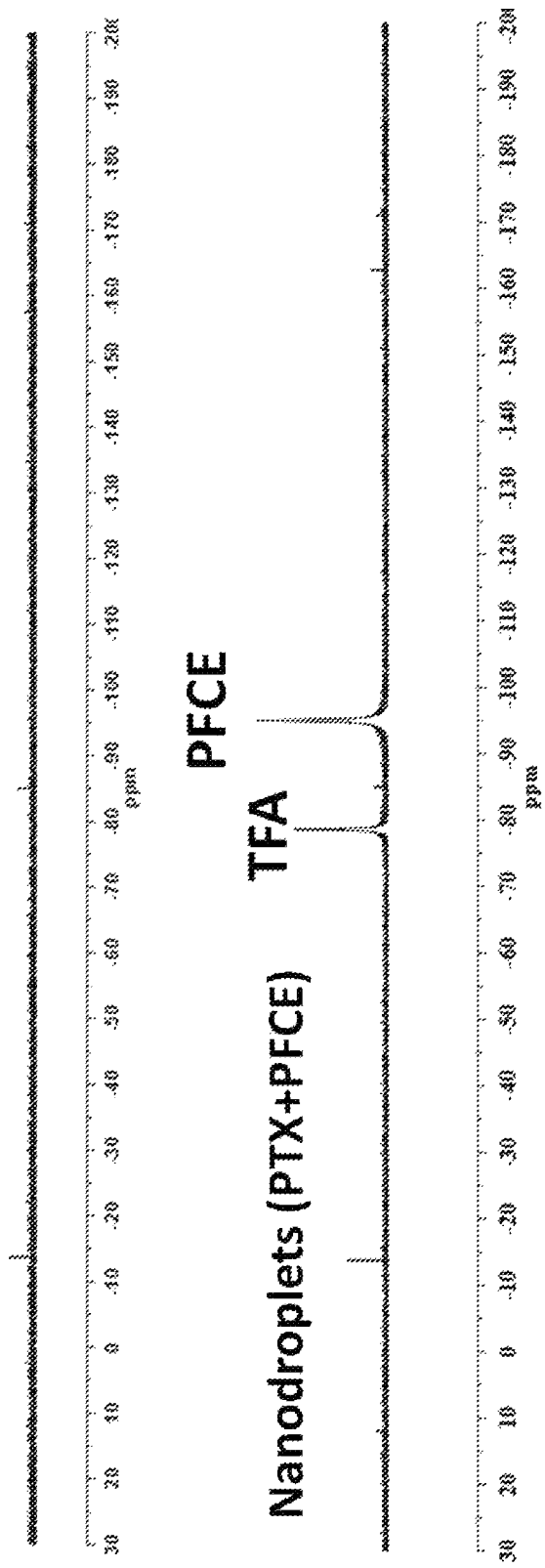
FIG. 9 shows the $^{13}$F NMR of nanodroplets, wherein the oil in the nanodroplet composition was MIGLYOL® 812 and perfluoro crown ether (PFCE) compared with MIGLYOL® 812 nanodroplets, wherein trifluoroacetic acid (TFA) used as internal reference.

In another experiment, the oil in the nanodroplet composition was MIGLYOL® 812 and perfluoro-15-crown-5-ether (PFCE) compared with MIGLYOL® 812 nanodroplets. The PFCE used in this case was 300 uL per 1.25 g mPEG-PDLLA. Fixed the same amount of mPEG-PDLLA, the PFCE can be ranged from 200 ul to 1 mL. FIG. 9 shows the $^{19}$F NMR of nanodroplets, which provides an unequivocal and unique opportunity for tracking and quantification of nanoparticles.

Comparison to Commercial Products

Figure 10:
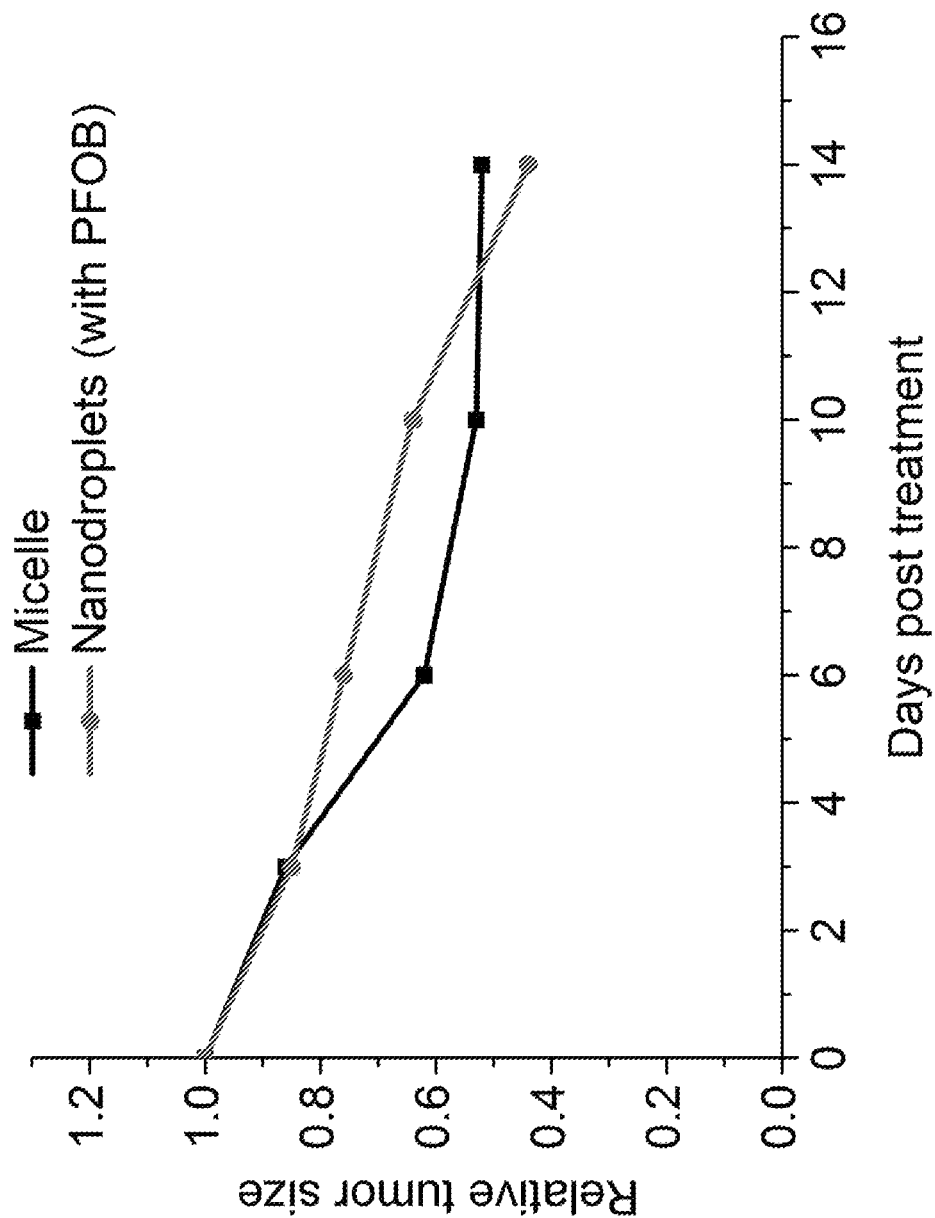
FIG. 10 shows a graph of relative tumor size for two treatment groups. MIA PaCa-2 cell suspensions were injected subcutaneously on the backs of mice to establish the tumor model. When tumor volume reached approximately 200 mm$^3$, groups of tumor-bearing mice (n=5) were injected through the tail vein twice per week with a dose of 0.7 mg paclitaxel (via nanodroplet formulation or via a micelle formulation that is an equivalent of GENEXOL® PM) per animal. Tumor size shrank in both groups but, at the end of two weeks, tumor size was smaller in the nanodroplet group than in the micelle group. The oil composition in the nanodroplets was MIGLYOL® 812 and PFOB.
Figure 11:
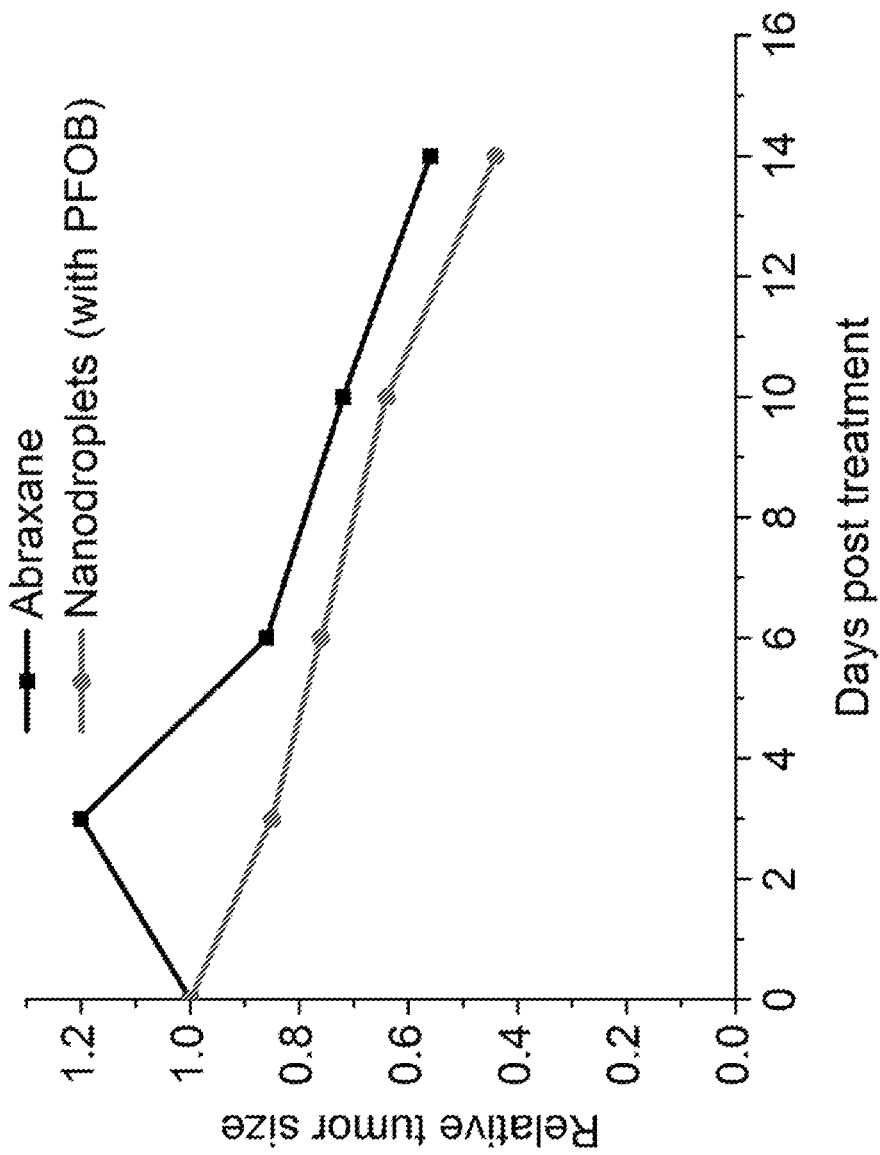
FIG. 11 shows a graph of relative tumor size for two treatment groups. MIA PaCa-2 cell suspensions were injected subcutaneously on the backs of mice to establish the tumor model. When tumor volume reached approximately 200 mm$^3$, groups of tumor-bearing mice (n=5) were injected through the tail vein twice per week with a dose of 0.7 mg paclitaxel (via nanodroplet formulation or via ABRAXANE®) per animal. Tumor size shrank in both groups but, at the end of two weeks, tumor size was smaller in the nanodroplet group than in the ABRAXANE® group. The oil composition in the nanodroplets was MIGLYOL® 812 and PFOB.

Two kinds of nanodroplets as described previously were evaluated alongside a GENEXOL® PM mimetic for tumor reduction abilities. Both nanodroplet formulations resulted in a greater decrease in tumor volume over a period of two weeks compared to the GENEXOL® PM-mimetic controls (FIGS. 5 and 10). Similarly, both formulations resulted in a greater decrease in tumor volume after four injections than the commercial product ABRAXANE®, which is a peptide-bound form of paclitaxel (FIGS. 6, 7, and 11). Thus, the nanodroplet formulations exhibit improved performance as compared to two different commercial products.

Even after injections stopped, tumor size continued to decrease, suggesting that nanodroplets accumulated at the tumor site during treatment and continued to supply the paclitaxel to kill tumor cells.

Throughout this publication, various publications are referenced. The disclosures of these publications in their entireties are hereby incorporated by reference into this application in order to more fully describe the methods, compositions, and compounds herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. One or more nanodroplets, each nanodroplet comprising
   (a) a copolymer comprising a hydrophilic block and a hydrophobic block, wherein the hydrophilic block of the copolymer is monomethoxy polyethylene glycol having a molecular weight from 1,500 Da to 2,500 Da and the hydrophobic block of the copolymer is poly (D,L-lactide) having a molecular weight from 1,500 Da to 2,500 Da;
   (b) a poloxamer having the formula

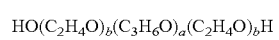

$HO(C_2H_4O)_b(C_3H_6O)_a(C_2H_4O)_bH$ wherein a is from 25 to 35 and b is from 70 to 80,
   (c) a hydrophobic core comprising an oil comprising a mixture of caprylic triglyceride and capric triglyceride,
   (d) an anti-cancer agent, and
   (e) a lyoprotectant,
   wherein
       the dry weight ratio of anti-cancer agent to the copolymer is from 1:5 to 1:9,
       the dry weight ratio of anti-cancer agent to the poloxamer is from 1:3 to 1:5,
       the weight ratio of oil to the copolymer is from 0.1 to 1,
       the dry weight ratio of lyoprotectant to the copolymer is from 0.1 to 1, and
       the nanodroplets have a Z-average diameter from 100 nm to 150 nm.

2. The one or more nanodroplets of claim 1, wherein the lyoprotectant comprises a sugar.

3. The one or more nanodroplets of claim 2, wherein the sugar comprises mannitol, sucrose, glucose, or any combination thereof.

4. The one or more nanodroplets of claim 2, wherein the sugar is mannitol.

5. The one or more nanodroplets of claim 1, wherein the anti-cancer agent comprises paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3 mercaptopropanol, progesterone, docetaxel, or any combination thereof.

6. The one or more nanodroplets of claim 1, wherein the anti-cancer agent is paclitaxel.

7. The one or more nanodroplets of claim 1, wherein each nanodrolet further comprises an anti-body drug conjugate.

8. The one or more nanodroplets of claim 7, wherein the anti-body drug conjugate is a maytansinoid, a dolastatin, an auristatin, a trichothecene, a calicheamicin, a duocarmycin, or any combination thereof.

9. The one or more nanodroplets of claim 1, wherein each nanodrolet further comprises a p-glycoprotein inhibitor.

10. The one or more nanodroplets of claim 9, wherein the p-glycoprotein inhibitor is verapamil, cyclosporin, tamoxifen, calmodulin antagonists, dexverapamil, dexniguldipine, valspodar (PSC 833), biricodar (VX-710), tariquidar (XR9576), zosuquidar (LY335979), laniquidar (R101933), elacridar (GF120918), timcodar (VX-853), taxifolin, naringenin, diosmin, quercetin, diltiazem, bepridil, nicardipine, nifedipine, felodipine, isradipine, trifluorperazine, clopenthixol, trifluopromazine, flupenthixol, emopamil, gallopamil, Ro11-2933, or any combination thereof.

11. The one or more nanodroplets of claim 9, wherein the p-glycoprotein inhibitor is tariquidar.

12. The one or more nanodroplets of claim 1, wherein each nanodrolet further comprises a perfluoro compound.

13. The one or more nanodroplets of claim 12, wherein the perfluoro compound is a fluoro ether.

14. The one or more nanodroplets of claim 13, wherein the fluoro ether is a perfluoro crown ether.

15. The one or more nanodroplets of claim 13, wherein the fluoro ether is perfluoro 12-crown-4 ether, perfluoro 15-crown-5 ether, perfluoro 18-crown-6 ether, perfluoro 20-crown-7 ether, perfluoro dibenzo-18-crown-6 ether, perfluoro diaza-18-crown-6 ether, or any combination thereof.

16. The one or more nanodroplets of claim 13, wherein the fluoro containing ether comprises perfluoro 15-crown-5 ether.

17. The one or more nanodroplets of claim 1, wherein each nanodrolet further comprises a dry powder.

18. A pharmaceutical composition comprising the one or more nanodroplets of claim 1 and a pharmaceutically acceptable carrier.

19. A method for treating cancer in a subject comprising administering to the subject the one or more nanodroplets of claim 1.

20. The method of claim 19, wherein the tumor or cancer is pancreatic cancer, lung cancer, breast cancer, ovarian cancer, prostate cancer, or colon cancer.

21. The method of claim 20, wherein the one or more nanodroplets are administered to the subject by intravenous injection.

22. The method of claim 21, wherein the dosage of the anti-cancer agent administered to the subject is from 30 mg/kg to 50 mg/kg per single administration.

23. The method of claim 19, wherein the one or more nanodroplets are administered to the subject at least two times per week.

24. A method for reducing a tumor in a subject comprising administering to the subject the one or more nanodroplets of claim 1.

* * * * *